United States Patent
Pflanz et al.

(10) Patent No.: US 9,017,995 B2
(45) Date of Patent: Apr. 28, 2015

(54) LIQUID-TRANSPORT AND ANALYTICAL TEST DEVICE

(75) Inventors: Karl Pflanz, Gleichen (DE); Eric Jallerat, Ville d/Avray (FR); Darius Haeusler, Northeim (DE); Markus Hollas, Wolfsburg (DE); Uwe Andag, Duderstadt (DE)

(73) Assignee: Sartorius Stedim Biotech GmbH (DE)

( * ) Notice: Subject to any disclaimer, the term of this patent is extended or adjusted under 35 U.S.C. 154(b) by 341 days.

(21) Appl. No.: 13/702,161

(22) PCT Filed: May 19, 2011

(86) PCT No.: PCT/EP2011/002500
§ 371 (c)(1),
(2), (4) Date: Dec. 5, 2012

(87) PCT Pub. No.: WO2011/154090
PCT Pub. Date: Dec. 15, 2011

(65) Prior Publication Data
US 2013/0078147 A1    Mar. 28, 2013

(30) Foreign Application Priority Data
Jun. 7, 2010    (DE) .......................... 10 2010 022 836

(51) Int. Cl.
*C12M 1/34* (2006.01)
*C12M 3/00* (2006.01)
(Continued)

(52) U.S. Cl.
CPC ....... *B01L 3/50273* (2013.01); *B01L 3/502769* (2013.01); *B01L 3/5023* (2013.01);
(Continued)

(58) Field of Classification Search
CPC .............. B01L 3/5027; B01L 3/50273; B01L 3/502769
USPC ........................................ 436/807; 435/288.5
See application file for complete search history.

(56) References Cited

U.S. PATENT DOCUMENTS

| | | |
|---|---|---|
| 6,420,622 B1 | 7/2002 | Johnston et al. |
| 2002/0082540 A1 | 6/2002 | Johnston et al. |

(Continued)

FOREIGN PATENT DOCUMENTS

| | | |
|---|---|---|
| DE | 102 24 568 | 2/2004 |
| DE | 10 2005 014 691 | 10/2006 |

(Continued)

OTHER PUBLICATIONS

International Search Report of Sep. 16, 2011.
(Continued)

*Primary Examiner* — Melanie Y Brown
(74) *Attorney, Agent, or Firm* — Gerald E. Hespos; Michael J. Porco; Matthew T. Hespos

(57) ABSTRACT

A liquid-transport device has a liquid-tight support (12) on which there is applied a start zone (24; 24') for applying transport liquid to be transported and a target zone (26, 28; 26*a-e*) into which the transport liquid is to be transported and also a conduction zone that extends between the start zone (24, 24') and the target zone (26, 28; 26*a-e*) and that has a microporous transport layer (14) in which the transport liquid flows by capillary force from the start zone (24; 24') to the target zone (26, 28; 26*a-e*). The conduction zone has a multiplicity of open flow channels separated from one another by microporous bridges having open-pored side walls.

11 Claims, 3 Drawing Sheets

(51) Int. Cl.
*B01L 3/00* (2006.01)
*G01N 33/558* (2006.01)
*G01N 30/00* (2006.01)

(52) U.S. Cl.
CPC ..... *B01L3/502715* (2013.01); *B01L 3/502723* (2013.01); *B01L 3/502746* (2013.01); *B01L 2200/027* (2013.01); *B01L 2300/0825* (2013.01); *B01L 2400/0406* (2013.01); *G01N 33/558* (2013.01); *G01N 30/00* (2013.01); *Y10S 436/807* (2013.01)

(56) References Cited

U.S. PATENT DOCUMENTS

2004/0022691 A1    2/2004    Allen et al.
2006/0205959 A1    9/2006    Moeller et al.
2007/0281353 A1*  12/2007    Vacanti et al. ............... 435/367

FOREIGN PATENT DOCUMENTS

| DE | 10 2007 036 906 | 11/2008 |
| EP | 1 542 010 | 6/2005 |
| EP | 1 608 974 | 10/2007 |
| WO | 01/02093 | 1/2001 |
| WO | 03/025573 | 3/2003 |
| WO | 2007/149043 | 12/2007 |

OTHER PUBLICATIONS

English Translation of the IPRP Chapter I PCT.

* cited by examiner

LIQUID-TRANSPORT AND ANALYTICAL TEST DEVICE

BACKGROUND OF THE INVENTION

1. Field of the Invention

The invention relates to a liquid-transport device comprising a liquid-tight support on which there is applied a start zone for applying transport liquid to be transported and a target zone into which the transport liquid is to be transported and also a conduction zone which extends between the start zone and the target zone and which comprises a microporous transport layer in which the transport liquid flows by capillary force from the start zone to the target zone.

2. Description of the Related Art

The invention further relates to an analytical test device using such a liquid-transport device.

Such liquid-transport devices and analytical test devices are known from US 2006/0205059 A1.

It discloses—in a specific embodiment—an analytical test device known in general as a lateral flow immunoassay.

The lateral flow test is based on capillary force-driven liquid transport in a thin layer of microporous, open-pored material. Microporous material is understood here to mean in general a material having a mean pore size of approximately 0.1 to 50 micrometers and a volume fraction of the pores of at least 30%. Cellulose nitrate applied to a liquid-tight support, for example a glass or plastic support, in a thin layer is typically used for this purpose. A liquid to be tested, which is referred to here as sample liquid or, neutrally, as transport liquid, is applied to the microporous layer at a designated site of the test device. This can, for example, be achieved by pipetting of the transport liquid or by dipping of certain areas of the test device into the transport liquid or by other means. The start zone is frequently supplemented with a sponge-type or nonwoven-type liquid reservoir to increase the liquid uptake capacity thereof, and in the context of the present invention it is only important that the microporous transport layer is contacted with the transport liquid only at one or more defined sites, viz., the start zone(s), at a given start time. In the lateral flow test, the start zone is typically covered with a selective binder, which can be a specific antibody against an analyte presumably contained in the transport liquid, such that the specific binder, in the dry state, is fixed in the start zone and, in the moistened state, i.e., after application of the transport liquid, is movable and can flow with said liquid. The selective binder is usually labeled with a detectable label, for example a fluorescent label, a gold or latex particle, a radioactive label, or by other means. As a result of binding of the selective binder to analyte actually contained in the transport liquid, the latter is thus labeled. By means of the capillary force in the microporous transport layer, the transport liquid, and with it the labeled analyte or free, selective binder, flows along the extension direction of the transport layer toward a predetermined target zone. The design of the target zone, including the number of target zones, depends on the purpose and design of the respective test. A target zone is frequently defined by the application of selective binders for the analyte that are immobilized in said zone. In the present context, immobilized means that the selective binders of the target zone are stationary both in the dry state and in the moistened state. The analyte already labeled with the selective binder of the start zone is bound to the immobilized selective binder of the target zone and thus fixed in the target zone. This is said to be a so-called sandwich reaction. This leads to an accumulation of the detectable label in the target zone. Such an accumulation normally only occurs when analyte is actually present in the transport liquid. Otherwise, the labeled selective binders of the start zone which are not bound to an analyte flow through the target zone. In such a test design, accumulation of the label in the target zone thus means the presence of analyte in the transport liquid. However, other types of target zones are also known. In so-called control zones, which are frequently downstream of the aforementioned first type of target zones, nonspecific binders for the selective binder of the start zone can be immobilized, and so in this second control zone there is an accumulation of label in any case of a successful test procedure. It is also possible to design target zones, depending on the setup of the test, such that the coloring thereof is precisely indicative of non-presence of analyte in the transport liquid.

In such lateral flow tests or, more generally, in such liquid-transport devices, as form the basis of customary lateral flow tests, there is a significant optimization dilemma. Firstly, very rapid liquid transport from the start zone to the target zone is desired. This is very important especially for tests in the home-care sector, in which the test is carried out by lay people. An example is the known pregnancy strip test. A transport layer having a very large pore size would be favorable with regard to maximum transport rate. The greater the pore size, the lower the flow resistance and the greater the resulting wetting rate, i.e., the transport rate of the transport liquid in the conduction zone. Therefore, in customary lateral flow tests, cellulose nitrate layers having a pore size of distinctly more than 3 micrometers are frequently used as transport layers. Secondly, a very small pore size is favorable with regard to optimization of the signal sharpness in the target zone. The smaller the pore size, the greater the inner surface area of the microporous layer, and the greater the inner surface area, the more selective binders which are immobilizable in the target zone, i.e., the more catchers for labeled analytes which are available in the target zone, leading to an all the more sharper signal. Lastly, a third parameter also has to be taken into consideration in the case of this optimization dilemma, viz., the thickness of the transport layer. A very large layer thickness would be desirable with regard to the optimization of the transport rate. However, a large layer thickness also means a large volume of the transport layer, which volume has to be filled by the transport liquid in order to realize a liquid flow. However, for many analytical tests, there is only a small amount of liquid available, and so it is necessary to keep losses to a minimum. Under this aspect, a low layer thickness would therefore be desirable.

The known liquid-transport devices and the analytical test devices based thereon do not really solve the described optimization dilemma. On the contrary, compromises suboptimal in all aspects are realized which, depending on the specific purpose of the application, more or less ignore one or the other of the above-described aspects.

WO 03/025573 A1 discloses a further lateral flow test having multiple start and target zones, wherein especially the latter can also be comprehended as an extensive target zone having a plurality of partial zones. Incidentally, the device of said document likewise contains the above-described disadvantages.

WO 2007/149043 A1 discloses an analytical test device which dispenses with microporous material as transport layer and as start zone and target zone. On the contrary, said device has a liquid-impermeable support having a multiplicity of macroscopic projections which are close to one another and which are likewise composed of liquid-impermeable material, which projections are so close to one another that a capillary force-driven flow of the transport liquid from the start zone into the target zone is produced. A disadvantage of this device is the low possibility of fixing a sufficient amount of catchers in the target zone and of labeled selective binders in the start zone owing to the small surface area available for adhesion. In addition, the open structure formed by the projections is extremely susceptible to evaporation, and this has to be considered disadvantageous with regard to using the transport liquid very sparingly.

DE 102 24 568 A1 discloses a miniaturized microtiter plate which consists of a liquid-impermeable support and of separate projections composed of microporous material that are applied thereto. The individual projections can be covered with different binders or chemicals. A liquid to be analyzed can be applied separately to the projections in a drop-by-drop manner and be reacted with the impregnation binder and the impregnation chemical. This realizes a so-called microarray, which allows the observation of a multiplicity of reactions in a very confined space that are running in a spatially separated manner and at the same time. The individual sponges are separated from one another by trenches which are intended to prevent liquid exchange between the individual projections.

DE 10 2005 014 691 A1 discloses a further microarray device in which so-called wells, i.e., pans, are cut into a layer composed of microporous material such that they are closely adjacent to one another. The pans are suitable for accommodating living cells, and the microporous wall material which, in each case, connects the pans of a group to one another is used to uniformly distribute nutrient liquid onto the pans. The transport of the nutrient liquid within a group of pans follows driven by the capillary force established by the micropores of the wall material. The nutrient solution is supplied to each group of pans by conventional microfluidics channels which are incorporated into the liquid-impermeable support material. Therefore, in the known device, no conduction zone which would comprise microporous material is involved in the transport of the liquid from the application site to the target site, i.e., to the particular group of pans.

It is an object of the present invention to develop a congeneric device such that the flow rate is sped up without simultaneous pore enlargement and without increase in membrane thickness.

SUMMARY OF THE INVENTION

This object is achieved by a liquid-transport device with a liquid-tight support on which there is applied a start zone for applying a transport liquid, a target zone to which the transport liquid is to be transported and a conduction zone that extends between the start zone and the target zone and which has a microporous transport layer in which the transport liquid flows by capillar force from the start zone to the target zone. The conduction zone has a multiplicity of open flow channels which are separated from one another by microporous bridges having open-pored side walls.

The preferred application of such a liquid-transport device is an analytical test device, more particularly an immunoassay, comprising an aforementioned liquid-transport device, wherein, in at least one target zone, a selective binder is permanently immobilized which is capable of selectively binding to a labeled analyte transported with the transport liquid from the start zone into the target zone. In this connection, it is especially favorable when, as in customary lateral flow tests, at least one start zone contains a labeled, selective binder which is immobilized in the dry state and movable in the wet state and which is capable of selectively binding to an analyte contained in the transport liquid.

The basis of the invention is the surprising finding that the speed of the wetting front of a transport liquid in a microporous transport layer can be distinctly increased by the transport layer having a multiplicity of flow channels which run substantially in the direction of the wetting front, provided that the side walls of the channels, unlike in known microfluidics channels, are not closed, but open-pored, i.e., constitute an unsealed entrance to the open-pored micropore system of the transport layer. The exact physical causes of this phenomenon have not yet been clarified. However, it is suspected that the wetting characteristics of, firstly, the channels acting as relatively broad capillaries and of, secondly, the capillary force-producing micropores of the transport layer interact here to intensify capillary force.

This invention allows the use of a comparatively small-pored material, which, owing to its large inner surface area, is suitable for an especially dense adhesion of selective binders as a prerequisite for a sharp signal in an analytical test device, but wherein the disadvantageous braking action on the flow rate that is associated with the small porosity of the transport layer in the prior art is rectified or even overcompensated by the channels according to the invention. This allows better solutions to be found to the described optimization dilemma between transport rate and signal sharpness.

By appropriate selection of the dimensions of the channels, more particularly in terms of their relation to the microporous bridges separating them, the resulting speed-up effect according to the invention can be varied in wide ranges. Specific, advantageous dimensions are therefore provided by preferred embodiments of the invention. This dependence of the speed-up effect on the relative dimensions is of great practical importance. If the transport liquid is especially viscous or if it contains solids, for example cells or cell fragments, the channels must be selected comparatively broadly in order to prevent clogging. Nevertheless, by means of appropriate dimensioning of the bridges, it is possible, however, for precisely the desired extent of the speed-up effect according to the invention and thus the run time to be set.

It has been found to be favorable when the width of the channels and of the bridges and also the height of the bridges and the depth of the channels, i.e., more particularly the height of the transport layer, are, in each case, between 5 micrometers and 100 micrometers. It is especially advantageous when the width of the channels is between 10 and 50 micrometers. As stated in more detail below on the basis of specific experimental measurements, relative dimensions of channels and bridges in which the width of the bridges corresponds to 0.5 to 5 times, more particularly 0.9 to 1.2 times, the width of the channels have been found to be especially advantageous.

As already mentioned above, the channels run substantially in the direction of the wetting front of the transport liquid in the transport layer. In this connection, "substantially" means that the channels do not have to run exactly along the straight lines between start zone and target zone, but rather that "indirect routes" such as wavy lines, zigzag patterns and the like can also be realized, provided that the substantial directional component of the entire channel points from the start zone to the target zone. However, a straight course of the channels will be favorable in most cases, more particularly in terms of manufacture. Irrespective of the specific course form of the individual channels, it has been found to be favorable when adjacent channels run in parallel to one another. In other words, the width of the bridge between two adjacent channels remains the same preferably across the length of the channels. As mentioned, the relative dimensions of bridges and channels have a substantial influence on the extent of the speed-up effect according to the invention. Parallel channels therefore lead to a uniform manifestation of the speed-up effect across the entire channel length.

Although it is conceivable in principle for the base of the channels, too, to have a thin layer of a microporous material, it has been found to be favorable when the base of the channels is formed by the liquid-impermeable support. A microporous base layer, which would have to be extremely thin in order for the total thickness of the microporous transport layer to be kept very low so as to conserve transport liquid, will hardly be expected to have a speed-up effect, as is the case for the channel side walls connected to the extensive body of the microporous transport layer. The unevennesses realized by the open pores of such a base layer will more likely have a braking action. Nevertheless, such realizations of the present invention are not excluded.

The liquid-transport device according to the invention can in principle be designed to be of any desired complexity. More particularly, it is not restricted to simple structures having only one start zone and one target zone having only one transport zone lying inbetween. On the contrary, it is also possible to realize variants in which a plurality of separate start zones connected to a common target zone by means of a plurality of separate conduction zones are applied to the support. Conversely, another possibility is that a plurality of separate target zones connected to a common start zone by means of a plurality of separate conduction zones are applied to the support. In this connection, it is not necessary for the respective conduction zones to run in parallel to one another. On the contrary, they can also run at an angle of other than zero degrees to one another. Also conceivable are intersections of conduction zones in which fractions of the transport liquid or of different transport liquids that have been hitherto separated are mixed. Lastly, it is also not necessary in the context of the present invention for exactly one conduction zone to be assigned to each pair of start zone and target zone. On the contrary, such a pair of start zone and target zone can be connected to one another by means of a plurality of separate conduction zones. For example, it is conceivable for the transport liquid to be supplied from a start zone to the target zone by routes differing in length or by routes having different channel widths.

Further features and advantages of the invention will be apparent from the following detailed description and the drawings.

DETAILED DESCRIPTION OF THE PREFERRED EMBODIMENTS

Figure 1:
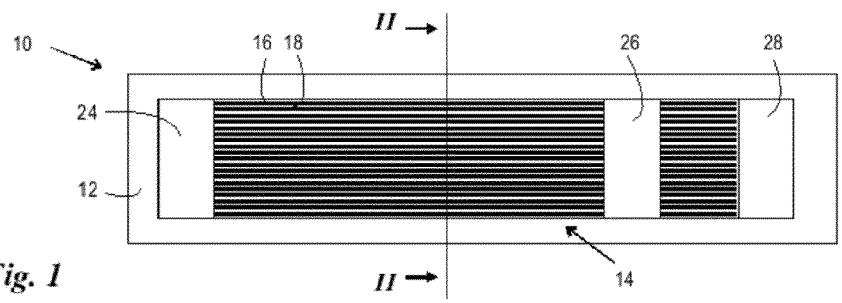
FIG. 1 is a diagrammatic top view of one embodiment of a test device according to the invention.
Figure 2:
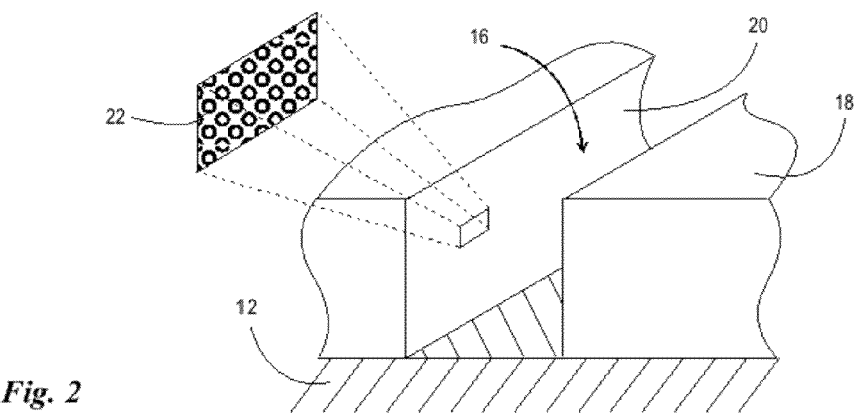
FIG. 2 is a tear-out diagram of the sectional view along the intersecting line II-II in FIG. 1.
Figure 3:
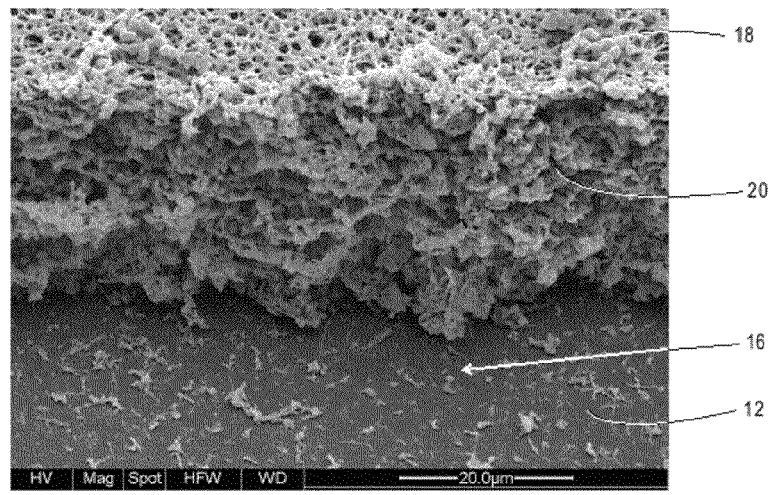
FIG. 3 is a scanning electron microscopy image of a channel structure according to the invention producible using a Nd:YVO4 solid-state laser.

FIG. 1 shows, in greatly diagrammatic form, a top view of a test device according to the invention. FIGS. 2 and 3 each show details of the device of FIG. 1. FIGS. 1 to 3 will be discussed together below.

The same reference symbols refer to the same or corresponding elements in all the figures.

The test device 10 according to FIG. 1 corresponds to known lateral flow assays in terms of its fundamental structure. The foundation of the device is a support 12, which, for example, is made of glass, more particularly borosilicate glass, plastic or another liquid-impermeable material, and generally a very low reactivity with constituents of the intended samples and reagents has to be ensured.

It will often be favorable to perform a surface functionalization, for example an aminosilane coating, of the support 12. The surface modification has the advantage that there is better adhesion of a microporous transport layer subsequently applied to the support. The microporous support layer used can be, for example, cellulose nitrate, polyamide, polysulfone, PVDF, porous ceramics and others.

In a preferred embodiment, a prefabricated microporous membrane, as microporous support layer, can be adhesively bonded/laminated onto the support 12 optionally modified as described above.

The microporous support layer can also consist of multiple materially different layers of the aforementioned materials or of materially identical layers differing in pore size distribution, and these multilayer structures can be applied to the support by "cocasting" methods known to a person skilled in the art.

One example is the application of a casting solution composed of a polymer blend of commercially available cellulose nitrate (5% to 10%) and optionally cellulose acetate (less than 2%) in a solvent mixture composed of methyl acetate (40%-60%), alcohols (30%-50%) and water. In addition, the casting solution can contain customary wetting agents to ensure reliable wetting, for example SDBS (sodium dodecylbenzenesulfonate) or SDS (sodium dodecyl sulfate), each in a proportion by weight of below 0.5%.

When drying the casting solution layer applied to the support 12, a porous transport layer 14 is produced under phase inversion with evaporation of the predominant constituents of the solvent mixture. The resulting thicknesses of the transport layer 14 are controlled by the coating thickness of the casting solution. Layer thicknesses of approximately 100 to 500 micrometers wet thickness result here in dry thicknesses of 10 to 100 micrometers. After drying of the transport layer 14, it is structured by removing the microporous layer in certain areas, producing a multiplicity of channels 16, between which bridges 18 composed of microporous material remain in each case. In this connection, as indicated diagrammatically in FIG. 2 by the enlarged cutout 22 and can be seen clearly in FIG. 3 in the scanning electron microscopy image, it should be ensured that the material pores on the surface of the channel walls 20, i.e., on the bridge sides, are not sealed, but remain open, allowing liquid from the channel to penetrate the microporous bridge material.

This is achieved, for example, by laser structuring with laser systems tailored to the particular transport layer material. For the cellulose nitrate layers explained in detail above as an example, a Nd:YVO4 solid-state laser having picosecond pulses, especially at a wavelength of 532 nanometers, and a pulse length of 12 picoseconds, a pulse energy of 10 microjoules and a pulse frequency of 10 kilohertz, whose beam has been focused onto the transport layer by means of a 100 millimeter F-theta lens and a feed rate of 25 millimeters per second, has been found to be suitable. By contrast, a CO2 laser in the infrared range, which resulted in fusion and thus in sealing of the channel wall pores, has been found to be unsuitable.

Figure 4:
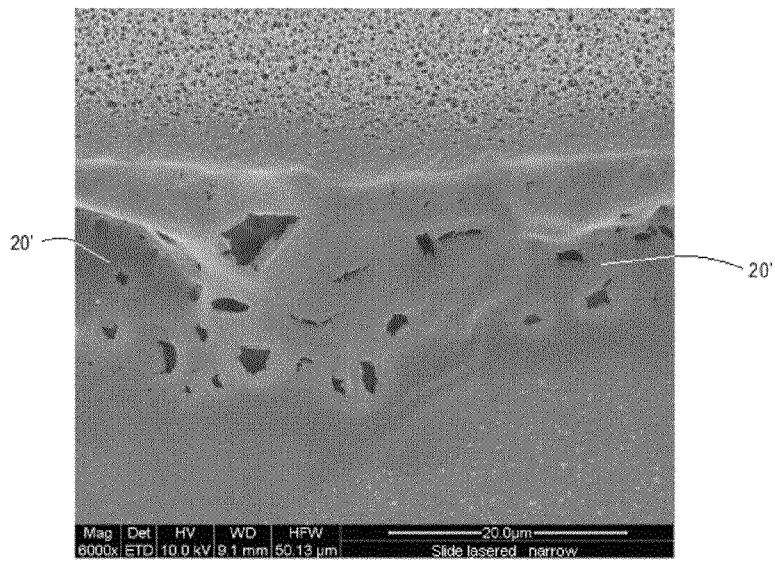
FIG. 4 is a scanning electron microscopy image of a channel structure producible using a CO2 laser in the infrared range, as comparative example.

According to FIG. 4, the use of a CO2 laser in the infrared range results in a channel structure which differs from the channel structure according to the invention of FIG. 3 in that it does not have any open-pored channel walls 20, but in that the channel walls 20' exhibit a largely closed structure having openings inhomogeneously distributed across the channel walls 20'.

As alternatives to laser structuring, it is, of course, also possible to use mechanical or chemical methods, more particularly etching methods. With respect to appropriate dimensioning of the channels 16 and the bridges 18, more detailed examples will be specified below.

In FIG. 1, a start zone 24 and two target zones 26, 28 have been further drawn in. The depiction thereof as rectangles having homogeneous surfaces is purely diagrammatic. Particularly the first target zone 26 can be designed to be optically indistinguishable from the structured transport layer 14. Preferably, it is merely defined by coverage of the porous material of the bridges in the first target zone 26 with immobilized, selective binders capable of fixing supplied, labeled analytes in the target zone 26. However, the start zone 24 and the second target zone 28 preferably comprise additional reservoir pads, for example in the form of glass-fiber nonwovens, which are connected to the transport layer 14 in a liquid-conducting manner. By this means, it is possible to deposit in the start zone a larger volume of sample liquid which is released continuously as transport liquid into the transport layer and flows in the direction of the target zones 26, 28 by means of the presumed interaction between the capillarities of the porous bridges and of the channels, as described above. The reservoir pad of the second target zone 28 is used to maintain the transport flow, even if the wetting front of the transport liquid has reached the downstream end of the transport layer 14.

The liquid-transport speed-up effect according to the invention will be evidenced below using selected examples. For this purpose, cellulose nitrate layers 14 differing in thickness were applied to borosilicate support 12 in the manner described in detail above and structured differently, i.e., with different channel and bridge widths, using the laser system described above as being preferred. The channel depth or bridge height corresponded in each case to the layer thickness, i.e., the channel base was formed in each case by the material of the support 12. After application of an aqueous solution in the start zone 24, the time required by the wetting front to cover a distance of 40 millimeters was measured. For comparison, a measurement on a liquid-transport device which was not structured, but otherwise identical, was carried out in each case. The tables below report the respective results:

TABLE 1

Migration rate of the wetting front in sec/40 mm,
Thickness of the transport layer: 70 micrometers
Reference (no structure): 250 sec/40 mm

| Channel width [μM] →: Bridge width [μM]: ↓ | 20 | 50 |
|---|---|---|
| 20 | 8 | — |
| 50 | — | 7 |
| 100 | 21 | — |
| 250 | — | 28 |

A distinct speeding up of the migration rate with respect to the unstructured reference is discernible. In the case of the same dimensioning of channels 16 and bridges 18, the speed-up effect according to the invention is distinctly more pronounced than in the case of wider dimensioning of the bridges 18 compared to the channels 16.

TABLE 2

Migration rate of the wetting front in sec/40 mm,
Thickness of the transport layer: 35 micrometers
Reference (no structure): 570 sec/40 mm

| Channel width [μm] →: Bridge width [μm]: ↓ | 20 | 50 |
|---|---|---|
| 20 | 12 | — |
| 50 | — | 15 |
| 60 | 22 | — |
| 100 | 36 | — |
| 150 | — | 31 |
| 250 | — | 54 |

The same effects and tendencies as in table 1 are discernible, and overall the reduced layer thickness results in slowing of the flow rate.

TABLE 3

Migration rate of the wetting front in sec/40 mm,
Thickness of the transport layer: 10 micrometers
Reference (no structure): >1800 sec/40 mm

| Channel width [μm] →: Bridge width [μm]: ↓ | 20 | 50 |
|---|---|---|
| 20 | 58 | — |
| 50 | — | 137 |
| 60 | 85 | — |
| 100 | 96 | — |
| 150 | — | 245 |
| 250 | — | 252 |

Within each of the same channel widths, the same tendencies as in tables 1 and 2 are again discernible. However, in the case of the particularly low thickness of the transport layer, as realized here, the influence of the absolute value of the channel width is distinctly greater than in the case of the larger layer thicknesses considered previously. The reference measurement was terminated after 30 min, since the migration rate of the wetting front was so low that meaningful applications are barely conceivable here. However, low layer thicknesses are precisely of interest for applications with low liquid amounts, and so the present invention is particularly valuable here.

Figure 5:
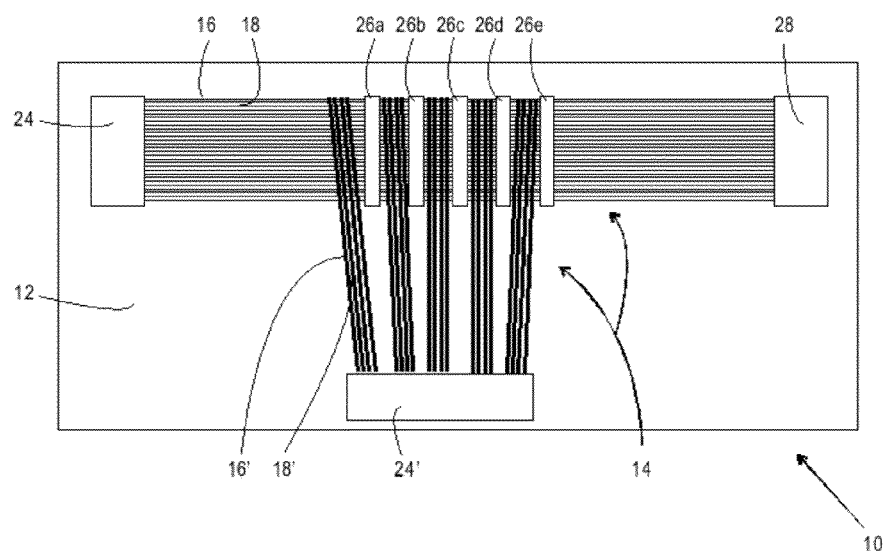
FIG. 5 is one embodiment of a test device according to the invention.

FIG. 5 shows a further embodiment of a test device according to the invention as a diagram. This is a bidirectional embodiment which, in contrast to the unidirectional embodiment of FIG. 1, exhibits two main directions of flow of transport liquid that are substantially perpendicular to one another. In addition to the start zone 24, there is a further start zone 24' on the support 12. In a first region, the transport layer 14 is structured comparably with the embodiment of FIG. 1, i.e., with straight, parallel channels 16 which extend from the start zone 24 to the second target zone 28 and pass a first target zone divided into five partial target zones 26a-e. In a second region, the transport layer 14 is structured into groups of channels 16' which again comprise in each case channels 16' running in parallel to one another and which extend from the additional start zone 24' into the immediate vicinity of the partial target zones 26a-e. As depicted diagrammatically, in the embodiment shown, the second channels 16' are made broader than the first channels 16, realizing in this region a transport structure which is more tolerant toward solids carried along in the transport liquid. To operate this device, a first liquid which contains particular reagents or washes out of the start zone 24 is applied in the start zone 24. A main flow to the second target zone 28 is realized by means of the channels 16. A second liquid, which can be a sample liquid for example, which contains solids such as cells or cell fragments is applied simultaneously, beforehand or later in the additional start zone 24'. By means of the channels 16', said liquid reaches the immediate vicinity of one of the first partial target zones 26a-e, specifically upstream thereof in each case with regard to the aforementioned main direction of flow. The difficult-to-transport liquid is thus conveyed by means of specifically dimensioned channels 16' to the first partial target zones 26a-e, where it can mix with the reagent solution supplied by means of the narrower channels 16. This mixing can, for example, result in an immunoreaction-mediated labeling of an analyte. The labeled analyte can be fixed in a known manner by appropriate immobilized binders in the first partial target zones 26a-e, and, despite the apparent undersizing of the channels 16, this is rapidly possible for the difficult-to-transport sample liquid owing to the very small distance to be bridged.

In the embodiment shown, the channels 16 and 16' intersect at the same level. This has the advantage that the entire channel/bridge structure of the device of FIG. 4 can be carved out from a common transport layer 14 with which support 12 was originally covered. However, in the context of the present invention, embodiments in which different channel groups do not intersect, but merely adjoin one another, are, of course, also possible. Also conceivable are variants in which different transport layer levels are realized.

Figure 6:
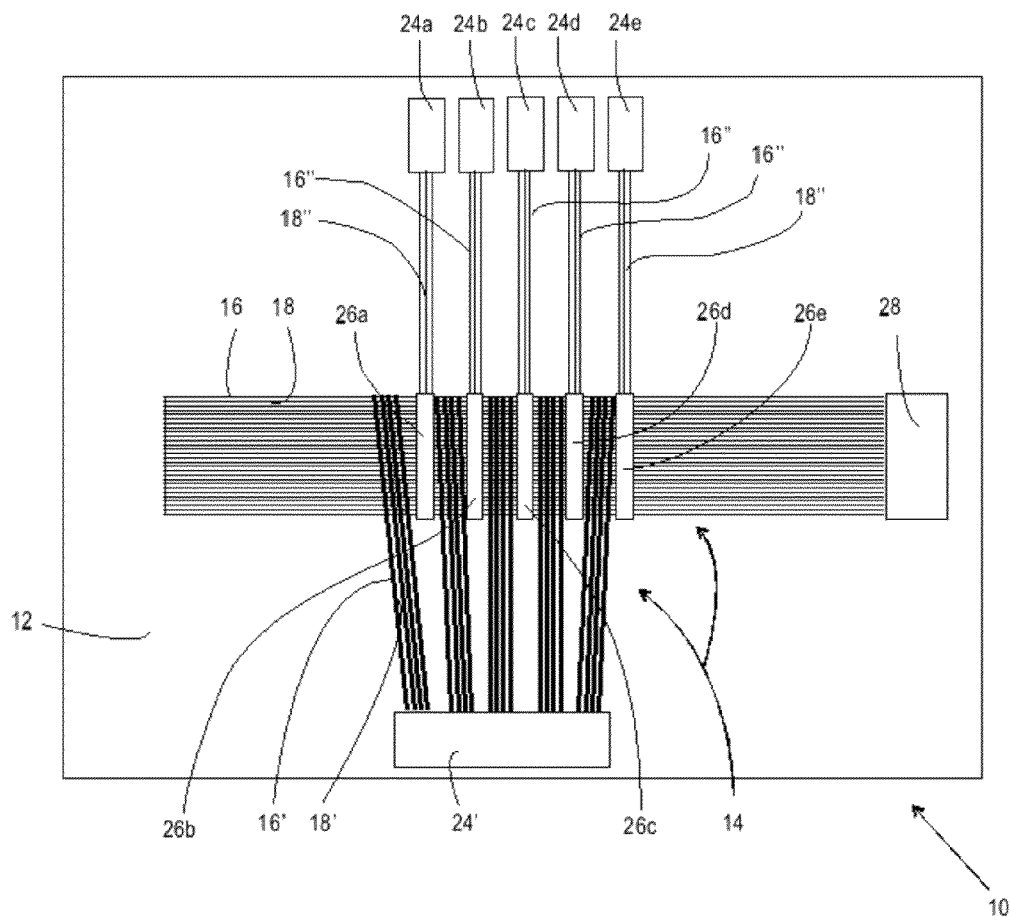
FIG. 6 is a further embodiment of a test device according to the invention.

A further variant, depicted in FIG. 6, of the embodiment according to FIG. 5 has, instead of the one start zone 24 in the left-hand region of the support 12 from FIG. 5, a plurality of start zones 24a-e which are in communication with the partial target zones 26a-e by means of multiple conduction routes comprising groups of channels 16" and bridges 18".

Alternatively, the plurality of start zones 26a-e can also be merged to form a single start zone connected in parallel to the partial target zones 26a-e by means of the aforementioned conduction routes.

It will be appreciated that the embodiments discussed in the specific description and shown in the figures are merely illustrative exemplary embodiments of the present invention. In the light of the present disclosure, a broad spectrum of possible variations is made available to a person skilled in the art. For example, he or she will adapt the choice of specific materials of the transport layer and of the support layer as well as the specific dimensions of bridges and channels and the fundamental course of the channel/bridge structures to his or her particular application.

The invention claimed is:

1. A liquid-transport device comprising a liquid-tight support (12) on which there is applied a start zone (24; 24') for applying transport liquid to be transported and a target zone (26, 28; 26a-e) into which the transport liquid is to be transported and also a conduction zone which extends between the start zone (24, 24') and the target zone (26, 28; 26a-e) and which comprises a microporous transport layer (14) in which the transport liquid flows by capillary force from the start zone (24; 24') to the target zone (26, 28; 26a-e), characterized in that the conduction zone has a multiplicity of open flow channels which are separated from one another by microporous bridges having open-pored side walls.

2. The liquid-transport device of claim 1, characterized in that the width of the channels (16; 16') and of the bridges (18; 18') and also the height of the bridges (18; 18') and the depth of the channels (16; 16') are, in each case, between 5 micrometers and 100 micrometers.

3. The liquid-transport device of claim 2, characterized in that the width of the channels (16; 16') is between 10 and 50 micrometers.

4. The liquid-transport device of claim 2, characterized in that the width of the bridges (18; 18') corresponds to 0.5 to 5 times the width of the channels (16; 16').

5. The liquid-transport device of claim 1, characterized in that the channels (16; 16') run parallel to one another.

6. The liquid-transport device of claim 1, characterized in that a base of the channels (16; 16') is formed by the liquid-impermeable support (12).

7. The liquid-transport device of claim 6, characterized in that a plurality of separate start zones connected to a common target zone by means of a plurality of separate conduction zones are applied to the support.

8. The liquid-transport device of claim 6, characterized in that a plurality of separate target zones (26, 28) connected to a common start zone (24) by means of a plurality of separate conduction zones are applied to the support (12).

9. The liquid-transport device claim 1, characterized in that the start zone (24') and the target zone (28) are connected to one another by means of a plurality of separate conduction zones.

10. An analytical test device, comprising the liquid-transport device claim 1, wherein, in at least one target zone (26, 28; 26a-e), a selective binder is permanently immobilized and is capable of selectively binding to a labeled analyte transported with the transport liquid from the start zone (24; 24', 24a-e) into the target zone (26, 28; 26a-e).

11. The analytical test device of claim 10, characterized in that at least one start zone (24; 24') contains a labeled, selective binder which is immobilized in a dry state and movable in a wet state and which is capable of selectively binding to an analyte contained in the transport liquid.

* * * * *